United States Patent [19]  [11]  4,285,928
Wada et al.  [45]  Aug. 25, 1981

[54] CONTRAST COMPOSITION FOR ANGIOGRAPHY

[75] Inventors: Juro Wada, 40-1, Haramachi-1-chome, Shinjuku-ku, Tokyo, Japan; Toshinari Itaoka, Tokyo, Japan

[73] Assignee: Juro Wada, Tokyo, Japan

[21] Appl. No.: 112,275

[22] Filed: Jan. 15, 1980

[30] Foreign Application Priority Data

Jan. 25, 1979 [JP] Japan .................................. 54-7437

[51] Int. Cl.³ ............................................. A61K 49/04
[52] U.S. Cl. ....................................................... 424/5
[58] Field of Search ............................................. 424/5

[56] References Cited

U.S. PATENT DOCUMENTS

| 3,867,431 | 2/1975 | Felder et al. | 424/5 |
|---|---|---|---|
| 3,962,439 | 6/1976 | Yokoyama et al. | 424/248 |
| 3,975,512 | 8/1976 | Long | 424/5 |
| 4,073,879 | 2/1978 | Long | 424/5 |

FOREIGN PATENT DOCUMENTS

| 1445925 | 8/1976 | United Kingdom | 424/248 |
|---|---|---|---|
| 1549038 | 7/1979 | United Kingdom | 424/248 |

*Primary Examiner*—Frederick E. Waddell
*Attorney, Agent, or Firm*—Cushman, Darby & Cushman

[57] ABSTRACT

A contrast composition for angiography comprising an emulsion containing an organic iodine compound as X-ray contrast agents and a perfluorocarbon compound having oxygen carrying ability.

2 Claims, No Drawings

CONTRAST COMPOSITION FOR ANGIOGRAPHY

This invention relates to contrast compositions for angiography and, more particularly, to contrast compositions comprising water-soluble contrast media for angiography admixed with a perfluorocarbon compound emulsion.

Contrast media are chemicals which enable morphologic and functional X-ray diagnosis of internal organs by establishing a difference in X-ray transmittance between the organs being observed and the surrounding tissues. They include positive contrast media and negative ones, the former being chiefly used at present for angiography. Above all, preparations containing organic iodine compounds as major constituents have been predominantly used.

Chemical stability, efficient excretion from the system, high tolerable dose, low viscosity, low irritating effect on the blood vessel, and low disturbing effect on liver or kidney, not to speak of high X-ray absorbance are indispensable to contrast media for angiography. A variety of contrast media for angiography have already been developed and showed considerable progress in contrasting ability and safety. Recently, preparations of triiodobenzoic acid derivatives have been in frequent use, but, among others, various diiodo compounds and monoiodo compounds have also been developed. However, the use of such contrast media accompanies many side effects, which cause a serious problem, such as vascular pain (burning sensation) in the injected blood vessel, oral burning sensation, bitter sensation, systemic feverish sensation, flushing, nausea, vomitting, abdominal pain, palpitation, oppressive sensation in the thorax, rash, etc. Above all, the vascular pain and related irradiation pain are symptoms developed in almost all cases and, although transient, are much annoying to the patient. Also, the nausea, vomitting, and abdominal pain occur as quite strong side effects and cannot be neglected, because the incidence amounts to 8 to 10% according to a report.

The vascular contrast media are required to be properly selected according to the region under examination. In contrasting a certain region such as, for example, coronary arteries, the retention of a contrast medium is tolerated only for several seconds. Particularly with respect to heart, arrhythmia and the decline in cardiac function are the side effects most frequently observed (these seem to occur because the patient falls into a state of cardiac arrest or a critical state of shock due to anoxia caused by the contrast medium). The incidence of such dangerous side effects leading to death has been reported to be 0.35%, so that a thorough preparative examination of the patient is necessary before the administration of a contrast medium.

As described above, conventional contrast media exert quite unnegligible side effects and a number of problems remain still unsolved inspite of the development of many new contrast media. At the present stage of development, main points to be improved are reduction of side effects, increase in tolerable dose, and extension of the duration of sustained administration.

Under the circumstances, the present inventors engaged in the improvement of vascular contrast media and conducted a large number of experiments. As a result, it was found surprisingly that the reduction in side effects and the administration of necessary amounts conforming to the object are possible by the addition of a perfluorocarbon compound emulsion having oxygen carrying ability to known contrast media. Based on this finding, preparation of the composition of this invention comprising a contrast medium and a perfluorocarbon compound emulsion has been accomplished.

An object of this invention is to provide a contrast composition for angiography comprising an emulsion containing an organic iodine compound as contrast media and a perfluorocarbon compound having oxygen carrying ability.

Other objects and advantages of this invention will become apparent from the following description.

The organic iodine compound for use in the composition of this invention can be any of those known as effective contrast agent for angiography and on the condition that the compound has a high iodine content in one molecule, high solubility in water, high intravascular stability and solubility, low viscosity, the excretion in high rate by kidney, no effect or very little effect, if any, on the circulatory system, and low tendency to combine with plasma proteins. Examples of such contrast media selected from commercial products are as shown in Table 1. These contrast media are generally available in the form of an aqueous solution containing a water-soluble salt of an organic iodine compound, such as sodium salt, methylglucamine salt, or a mixed salt thereof. Such an aqueous preparation has an iodine content of 250 to 500 mg/ml, a viscosity (in cps at 37° C.) of 5 to 11, and an iodine compound content of 20 to 85%.

TABLE 1

| Common name | Structural formula and composition | Trade name (supplier) | Content and dosage form |
| --- | --- | --- | --- |
| Methiodal sodium NF USP NNR 1952 | $ICH_2SO_3Na$ Sodium iodomethane sulfonate; aqueous solution | Abrodil (Bayer, Jap.) Methiodal Guerbet (Kodama, Jap.) Abrosil (Bayer, Ger.) Skiodan (Winthrop, US.) | Injection 20% 10 ml |

TABLE 1-continued

| Common name | Structural formula and composition | Trade name (supplier) | Content and dosage form |
|---|---|---|---|
| Iodopyracet diethanolamine salt USP BP | 3,5-Diiodo-4-pyridone N-acetic acid diethanolamine | Per-Abrodil (Bayer, Ger.) Diodrast (Winthrop, US.) Neo-Skiodan (Winthrop, US.) Diodone (Guerbert, Fr.) Pyelosil (Glaxo. Brit.) | Injection 70% 5 ml 70% 30 ml 35% 30 ml |
| Iodopyracet methylglucamine salt (Iodopyracet methylglumine salt) | 3,5-diiodo-4-pyridone-N-acetic acid N'-methylglucamine salt; aqueous solution | Per-Abrodil M (Yoshitomi-Bayer, Jap.) Glucadiodone (Guerbert, Fr.) Per-Abrodil (Bayer, Ger.) | Injection 45% 10 ml 60% 20 ml 80% 10 ml 80% 20 ml |
| Sodium acetrizoate BP NND 1964 | Sodium 3-acetylamino-2,4,6-triiodobenzoate; aqueous solution | Diaginal (Banyu, Jap.) Acetiodone (Guerbert, Fr.) Urokon Sodium (Mallinkrodt, US.) Tri-Abrodil (Bayer, Ger.) Triopac (Cilag, Swit.) | Injection 30% 25 ml 70% 25 ml |
| Sodium metrizoate | Sodium 3-acetamido-2,4,6-triiodo-5N-methyl acetamido benzoate Triodil  Na salt : Mg salt : Ca salt = 69 : 2.5 : 3.5 Isopaque 370  Na salt : Mg salt : Ca salt = 10.1 : 65.7 : 1.13 Isopaque 280  Mg salt : Ca salt = 59.1 : 1.13 Aqueous solution of a mixture of methylglucamine salt and sodium salt of acetrizoic acid Na salt:MeG salt = 1:4 | Triodil 75 (Glaxo, Brit.) Isopaque 370 (Winthrop, US.) Isopaque 280 (Winthrop, US.) Urokolin (Dai-ichi, Jap.) Vesamine (Gulden, Ger.) | Injection 75% 20 ml Injection 76% 20 ml Injection 60% 20 ml Injection 60% 20 ml 75% 20 ml |
| Sodium diatrizoate BP USP NND 1964 | Sodium 3,5-Diacetamido-2,4,6-triiodobenzoate; aqueous solution | Hypaque Sodium (Winthrop, US.) | Injection 50% 30 ml |

TABLE 1-continued

| Common name | Structural formula and composition | Trade name (supplier) | Content and dosage form |
|---|---|---|---|
| Meglucamine diatrizoate | $H_3COCHN$–[benzene ring with I, I, I, NHCOCH_3]–$CH_3$, COONH_2, CH_2(CHOH)_4CH_2OH<br><br>Methylglucamine 3,5-diacetamido-2,4,6-triiodobenzoate; aqueous solution | Cardiografin (Squibb, US.) <br> Angiografin (Schering, Germ. & Brit.) <br><br> Angiografin (Schering, Jap.) | Injection 85% 50 ml <br><br><br><br> Injection 65% 10 ml 20 ml 50 ml |
|  | Aqueous solution containing methylglucamine salt and sodium salt of diatrizoate<br>    Na salt:Meg salt = 10:66<br><br>Hypaque M:<br><br>    Na salt:Meg salt = 1:2<br>    Na salt:Meg salt = 40:18<br><br>    Na salt:Meg salt = 10:66 | Urografin (Schering, Jap.) (Squibb, US.) <br> Renografin (Squibb, US.) <br> Hypaque M (Winthrop, US.) <br><br> Urografin (Schering AG, Ger.) <br> Urovison (Schering, Jap.) <br> Urotrast (Mochida, Jap.) <br><br> Urotrast (Krka, Yugoslavia) | Injection 60% 20 ml <br> 60% 100 ml <br> 76% 20 ml <br><br><br><br> Injection 56% 25 ml <br> Injection 60% 20 ml <br> 75% 20 ml |
| Sodium iothalamate USP | $H_3COCHN$–[benzene ring with I, I, I, CONHCH_3]–COONa<br><br>Sodium-5-acetoamido-N-methyl-2,4,6-triiodo-isophthalamate; aqueous solution | Angio-Conray (Mallinckrodt, US.) <br> Conray 400 (Dai-ichi, Jap.) <br> (Mallinckrodt, US.) | Injection 80% 20 ml <br> Injection 66.8% 20 ml |
| Meglucamine iothalamate | $H_3COCHN$–[benzene ring with I, I, I, CONHCH_3]–COO–N$^+$H_2, CH_3, CH_2(CHOH)_4CH_2OH<br><br>Methylglucamine 5-acetamido-2,4,6-triiodo-isophthalamate; aqueous solution | Conray (Mallinckrodt, US.) <br> DIP Conray (Dai-ichi, Jap.) | Injection 60% 20 ml <br> Injection 30% 220 ml |
| Meglucamine iodamide | [benzene ring with COOH, I, I, I, CH_3COHN, CH_2NHCOCH_3]<br><br>3-Acetamido methyl-5-acetamide-2,4,6-triiodobenzoic acid<br>Methylglucamine salt of iodamide<br>Aqueous solution of a mixture of methylglucamine salt and sodium salt of iodamide in a ratio of 86:14 | Conraxin L (Takeda, Jap.) <br> Uromiro (Dr. FranzKohler Chemie, Ger.) <br> Conraxin L (DIP) (Takeda, Jap.) <br> Conraxin D (DIP) (Takeda, Jap.) <br> Conraxin H (Takeda, Jap.) | Injection 64.9% 20 ml <br><br><br> 100 ml <br><br> Injection 32.45% 200 ml <br> Injection 80% 20 ml |

The contrast composition of this invention can be prepared by adding one of the iodine compounds illustrate in Table 1 directly to a perfluorocarbon emulsion having oxygen carrying ability or more conveniently by intermixing, before use or in advance, a commercially available preparation of contrast medium containing said compound and a perfluorocarbon emulsion in a ratio suitable for the intended use.

Regarding the perfluorocarbon compound emulsion, a large number of preparations have been proposed as a blood substitute. According to this invention, any liquid perfluorocarbon preparation can be used without particular restriction so far as the preparation possesses a particle size suitable for administration into human blood vessels and has neither a tendency to accumulate in internal organs nor a disturbing effect on the organs or blood stream.

Desirable emulsions are those prepared by emulsifying, to a particle size of 0.3μ or less, perfluororcarbons having 9 to 11 carbon atoms and perfluorocarbon compounds of tertiary amines, each alone or in suitable mixtures, in the presence of a high-molecular nonionic surface active agent and/or a phospholipid as emulsifier and, if necessary, a fatty acid compound (in the form of free acid, alkali metal salt, or monoglyceride) having 8 to 22 carbon atoms, as auxiliary emulsifier. Detailed description of such emulsions may be found, for example, in Japanese Patent Application Laid-open No. 69,219/1975; No. 96,722/1977, U.S. Pat. No. 3,962,439, United Kingdom Pat. Nos. 1,445,925 and 1,549,038.

Examples of perfluorocarbon compounds suitable for use include those having 9 to 11 carbon atoms such as perfluorocycloalkanes, perfluoroalkylcycloalkanes, perfluorocyclohexane, perfluorodecalin, perfluoroalkyldecalines, perfluoroalkyltetrahdydropyranes, perfluoroalkyltetrahydrofurans, perfluoroalkanes, perfluoro-tert-alkylamines, perfluoro-N,N-dialkylcyclohexylamines, perfluoroalkylpiperidines, perfluoroalkylmorpholines, perfluoroadamantane, and perfluoroalkyladamantanes. Particularly preferred are those emulsions containing perfluorohydrocarbons as major constituents and perfluoro-tert-amines as minor constituents which form no precipitate on the addition of a plasma expander such as dextran, hydroxystarch, and modified gelatins (Japanese Patent Application Laid-open No. 96,722/1977, U.K. Pat. No. 1,549,038). The perfluoro-tert-amine can be replaced by an organic hydrocarbon adamantane or an alkyl derivative thereof.

The emulsifiers for use in the emulsions are high-molecular nonionic surface active agents having a molecular weight of about 2,000 to about 20,000 such as, for example, polyoxyethylene-polyoxypropylene copolymers, polyoxyethylene alkyl ethers, and polyoxyethylene alkylaryl ethers and/or phospholipids such as yolk lipids and soybean lipids.

The fatty acid compounds used as auxiliary emulsifiers are fatty acids having 8 to 22 carbon atoms and physiologically acceptable sodium and potassium salts or monoglycerides thereof such as, for example, caprylic acid, capric acid, lauric acid, myristic acid, palmitic acid, stearic acid, behenic acid, palmitoleic acid, oleic acid, linolic acid, arachidonic acid, sodium or potassium salts thereof, and monoglycerides thereof. These fatty acid compounds are used each alone or in mixtures of two or more.

Of the emulsions most preferred are those containing 95 to 50 parts by weight of perfluorodecalin or perfluoromethyldecalin and 5 to 50 parts by weight of a perfluoro-tert-amine selected from the group consisting of perfluoro-N-($C_4$-$C_6$)alkylpiperidines, perfluoro-N-($C_5$-$C_7$)alkylmorpholines and perfluoro-tert-($C_5$-$C_7$)alkylamines, or perfluoroadamantane.

An aqueous emulsion containing 10 to 50% (W/V) of a perfluorocarbon, 2.0 to 5% (W/V) of an emulsifier, and, if necessary, 0.1 to 1.0% (W/V) of a phospholipid and 0.004 to 0.1% (W/V) of a fatty acid compound as emulsifying adjuvants is mixed with a physiological aqueous solution such as a high tonic electrolyte solution comprising 3 to 7% of NaCl, 0.15 to 0.4% of $CaCl_2$, 0.1 to 0.5% of $MgCl_2$, 0.7 to 2.0% of D-glucose, 0.3 to 0.5% of KCl, 2 to 4% of $NaHCO_3$, and, if necessary, a plasma expander to adjust the emulsion to become physiologically isotonic. If necessary, the resulting emulsion is further corrected with a buffer solution to allow for the mixing with a contrast medium (correction by taking into account the EDTA content of the contrast medium).

The mixing of a water-soluble vascular contrast medium and a perfluorocarbon compound emulsion is performed in advance or just before use. The ratio of an organic iodine compound to a perfluorocarbon is in a wide range of from 0.17:1 to 16:1. The concentrations of both components in the contrast composition for angiography of this invention are 5 to 80% (W/V) for the organic iodine compound and 5 to 30% (W/V) for the perfluorocarbon compound. For instance, in mixing Urografin (76%) with a perfluorocarbon emulsion (35%), a ratio of 0.1–9 (Urografin):1 (perfluorocarbon emulsion), preferably 0.25–4:1 is used. The particle size of the perfluorocarbon is maintained at 0.05 to 0.3μ after mixing.

Before use, 100% oxygen is bubbled through the contrast composition of this invention to charge the medium with oxygen. In contrasting the cardiac blood vessels of a seriously cyanotic patient suffering from, for example, troubles of coronary arteries such as acute myocardial infraction, angina pectories, etc., and further anomalous drainage of the pulmonary veins, the concentration of a fluorocarbon compound emulsion is increased to approach a ratio of 0.1:1 (in this case the decrease in contrasting ability caused by the decrease in the proportion of a contrast medium can be replenished by the increase of dosage). In normal cases, there is usually used a ratio (approaching 9:1) which ensures sufficient supply of oxygen and is effective in controlling the vascular pain. The ratio can be varied widely within the above-noted range according to the purpose of vascular contrasting.

The method of administering the contrast composition of this invention is as described below.

The contrast agent for the contrast composition is properly selected according to the region being examined. The method of administration varies with the region being examined. In contrasting the arteries and veins in the limbs, the contrast composition is injected into the blood vessel by cutaneous puncture. To contrast the soracic and abdominal aortae or branches thereof, the composition is injected into the blood vessel by cutaneous puncture or by catheterization through the femoral arteries. For the contrasting of cardiopulmanary blood vessels, the composition is administered by injection into the anconeal veins by cutaneous puncture or by cardiac catheterization. The dose is 5 to 100 ml each time and can be administered rapidly in a short period or in a sustained manner as the occasion demands but quite independent of the region being contrasted or the quantity to be administered.

The contrast composition for angiography of this invention permits the administration of a large quantity of a contrast agent over a long period of time while keeping the patient from the arrest of organ functions (e.g. cardiac arrest) or the incidence of severe shock due to anoxia by the supply of oxygen by perfluorocarbons.

the method of preparation, effect in comparison with other preparations, and safety of the contrast composition of this invention are further illustrated below with reference to examples.

PREPARATION EXAMPLE 1

A perfluorocarbon emulsion comprising 30.4% of perfluorodecalin, 5% of perfluorotripropylamine, 3.4% of a polyoxyethylene-polyoxypropylene copolymer ("PLURONIC F68"; average molecular weight 8,350), 0.6% of egg yolk lipid, 0.004% of potassium oleate, 6% of NaCl, 2.1% of NaHCO$_3$, 0.336% of KCl, 0.42% of MgCl$_2$, 0.356% of CaCl$_2$, and 1.8% of D-glucose was prepared and thermally sterilized. The average particle size was 0.09 to 0.1μ. This emulsion was very stable and showed no agglomeration of particles after 6 months of storage at 4° C. The mixing of the emulsion with contrast media was performed in advance or just before use. The contrast medium employed was a commercial aqueous solution ("Urografin" 76% solution) containing a mixture of sodium salt and methylglucamine salt of diatriazoate [iodine content, 37.03%; viscosity, 7.3 cps at 37° C.; specific gravity at 20° C., 1.422; pH, 7.2–7.6; containing, in 1 ml, 597.30 mg of amidotrizoate (as anhydrous substance), 6.29 mg of sodium hydroxide and 159.24 mg of meglumine]. Five parts by volume of this solution and 2 parts by volume of the above perfluorocarbon compound emulsion were mixed and homogenized to obtain a clinically usable contrast composition.

PREPARATION EXAMPLE 2

A constrast composition was prepared by repeating the procedure of preparation Example 1, except that the emulsion contained a mixture of 17.5% of perfluorodecalin and 17.5% of perfluoroadamantane in place of 30.4% of perfluorodecalin and 5% of perfluorotripropylamine.

PREPARATION EXAMPLE 3

A contrast composition was prepared by repeating the procedure of Preparation Example 1, except that the emulsion contained 3.4% of a polyoxyethylene octyl ether having a molecular weight of 3,500 in place of 3.4% of PLURONIC F68.

PREPARATION EXAMPLE 4

A contrast composition was prepared by repeating the procedure of Preparation Example 1, except that the emulsion contained 35% of perfluorodecalin and 3.4% of egg yolk lipid in place of 30.4% of perfluorodecalin, 5% of perfluorotripropylamine, 3.4% of a polyoxyethylene-polyoxypropylene copolymer (PLURONIC F68), and 0.6% of egg yolk lipid.

PREPARATION EXAMPLE 5

Contrast compositions were prepared by repeating the procedure of Preparation Example 1, except that the emulsion contained perfluorobutylcyclohexane, perfluorotrimethylcyclohexane, perfluoroethylpropylcyclohexane, perfluoromethyldecalin, perfluorohexyltetrahydropyrane, perfluoropentyltetrahydrofuran, perfluorohexyltetrahydrofuran, or perfluorodecane in place of perfluorodecalin.

PREPARATION EXAMPLE 6

Contrast compositions were prepared by repeating the procedure of Preparation Example 1, except that the emulsion contained perfluoro-N,N-dibutylmonomethylamine, perfluoro-N,N-diethylpentylamine, perfluoro-N,N-dipropylbutylamine, perfluorotripropylamine, perfluoro-N,N-diethylcyclohexylamine, perfluoro-N-pentylpiperidine, perfluoro-N-hexylpiperidine, perfluoro-N-butylpiperidine, perfluoro-N-pentylmorpholine, perfluoro-N-hexylmorpholine, or perfluoro-N-heptylmorpholine in place of perfluorotripropylamine.

PREPARATION EXAMPLE 7

A contrast composition was prepared by repeating the procedure of Preparation Example 1, except that the emulsion contained a polyoxyethylene-polyoxypropylene copolymer having an average molecular weight of 15,800 in place of that having an average molecular weight of 8,350.

PREPARATION EXAMPLE 8

Contrast compositions were prepared by repeating the procedure of Preparation Example 1, except that there was used, as the contrast medium, in each case one of the commercial preparations of meglucamide iodamide (Conraxin L, Takeda), iodopyracet methylglucamine salt (Perabrodil M, Yoshitomi-Bayer), sodium acetrizoate (Diadinol, Banyu), sodium metrizoate (Urokolin M, Dai-ichi), meglucamine diatriazoate (Angiografin, Japan Schering), sodium iothalamate (Conray 400, Dai-ichi), and meglucamine iothalamate (DIP Conray, Dai-ichi) in place of Urografin 76% solution.

PREPARATION EXAMPLE 9

A contrast composition was prepared by repeating the procedure of Preparation Example 1, except that the mixing ratio of the perfluorocarbon compound emulsion to the contrast medium was 1 part by volume to 5 parts by volume.

Comparative Experimental Example

Selective coronary contrasting was performed on a male beagle, about 20 kg in body weight, by using a contrast composition for angiography prepared in Preparation Example 1, which had been saturated with oxygen, and a control composition containing a contrast medium alone (Urografin 76%). Fifty cubic centimeters of the contrast composition was injected at a rate of 0.4 to 0.6 ml/second into the left coronary artery by means of an automatic injection device under application of an air pressure. In the case of control composition, perfect ventricular fibrillation was developed in a retention period of 15 seconds and followed by cardiac deth, whereas the vascular contrast composition of this invention showed no side effect in a retention period of 60 seconds, thus ensuring the contrasting to last for a period of 60 seconds, which corresponds to at least a fourfold extension of the contrasting time in prior art. The electrocardiogram and the blood pressure showed no noteworthy abnormality during 30 minutes after injection of the contrast composition of this invention.

Acute toxicity test

An acute toxicity test was performed on the contrast composition prepared in Preparation Example 1 by using male mice (each 18 to 25 g in body weight) of the DD-strain. A predetermined dose shown in Table 2 was manually injected at a rate of 2 ml/minute into the coccygeal vein (vena coccygea) of each member of a group of 10 mice. Observation was continued during one week after the injection and LD$_{50}$ was calculated. The results obtained were as shown in Table 2.

The LD$_{50}$ values of the perfluorocarbon emulsion (containing 35% of perfluorocarbon) and Urografin 76% (a solution containing a mixture of meglucamine salt and sodium salt of diatrizoate) have been known to be about 130 ml/kg (about 45.5 g/kg body weight in terms of perfluorocarbon) and about 19 g/kg body weight in terms of the mixture of meglucamine salt and sodium salt of diatrizoate, respectively. Under the testing conditions herein used, these $LD_{50}$ values were found to be 45 g/kg body weight in terms of perfluorocarbon and 17.5 g/kg body weight in terms of the mixture of meglucamine salt and sodium salt of diatrizoate, respectively.

From the results shown in Table 2, $LD_{50}$ of the contrast composition was found to be 34.7 ml/kg body weight (that is, 18.8 g/kg body weight in terms of the mixture of meglucamine salt and sodium salt of diatrizoate), indicating that there is no enhancement of the acute toxicity attributable to the mixing of a contrast medium with a perfluorocarbon emulsion. Similar tests to that described above were performed with respect to meglucamine iothalamate and meglucamine iodamide in addition to Urografin 76% and no extraordinary change due to the mixing with the perfluorocarbon emulsion was found.

TABLE 2

| Dose (ml/kg body weight) | Day | | | | | | |
|---|---|---|---|---|---|---|---|
| | 1 | 2 | 3 | 4 | 5 | 6 | 7 |
| 20 | 10/10 | 10/10 | 10/10 | 10/10 | 10/10 | 10/10 | 10/10 |
| 24 | 10/10 | 9/10 | 9/10 | 9/10 | 9/10 | 9/10 | 9/10 |
| 28.8 | 8/10 | 6/10 | 6/10 | 6/10 | 6/10 | 6/10 | 6/10 |
| 34.6 | 5/10 | 4/10 | 4/10 | 4/10 | 4/10 | 4/10 | 4/10 |
| 41.5 | 3/10 | 3/10 | 3/10 | 3/10 | 3/10 | 3/10 | 3/10 |
| 49.8 | 2/10 | 1/10 | 1/10 | 1/10 | 1/10 | 1/10 | 1/10 |

As described in the foregoing, the contrast composition for angiography according to this invention shows reduced side effects on administration and, hence, an increased tolerable dose and permits the angiography over a prolonged period of time without developing abnormality in the electrocardiogram and any decrease in blood pressure, thus contributing greatly to the progress in the field of angiography. Particularly in the case of selective coronary contrasting, the instant injection of 5 to 10 ml of a conventional contrast medium will cause a decline in cardiac function which may be fatal, whereas the composition of this invention permits the contrasting of coronary arteries to last for about 2 minutes by sustained injection, because the ratio between the perfluorocarbon compound and the contrast medium can be varied in accordance with the condition of coronary arteries.

What is claimed is:

1. A physiologically isotonic contrast composition for angiography comprising an emulsion containing an organic iodine compound as X-ray contrast agents and a perfluorocarbon compound having oxygen carrying ability, the organic iodine compound being at least one of sodium iodomethane sulfonate, 3,5-diido-4-pyridone-N-acetic acid diethanolamine, 3,5-diido-4-pyridone-Nacetic acid-N'methylglucamine salt, sodium 3-acetylamino-2,4,6-triiodobenzoate, sodium 3-acetamido-2,4,6-triiodo-5-N-methyl acetamido benzoate, mixture of of methyl glucamine salt and sodium salt of diatriazoate, sodium-5-acetamido-N-2,4,6-triiodo-isophthalamate, methyl glucamine-5-acetamido-2,4,6-triiodoisophthalamate or 3-acetamido methyl-5-acetamide-2,4,6-triiodobenzoic acid methyl glucamine salt and methylglucamine salt of iodamine, the perfluorocarbon compound being a mixture comprising 95 to 50 parts by weight of at least one member of the group consisting of perfluorodecalin and perfluoromethyldecalines and 5 to 50 parts by weight of at least one of perfluorotripropylamine, perfluoro-N,N-dibutylmonomethylamine, perfluoro-N,N-diethylpentylamine, perfluoro-N,N-dipropylbutylamine, perfluoro-tripropylamine, perfluoro-N,N-diethylcyclohexylamine, perfluoro-N-butylpiperidine, perfluoro-N-pentylmorpholine, perfluoro-N-hexylmorpholine, perfluoro-N-heptylmorpholine, and perfluoroadamantane, the concentration of the organic iodine compound being 5 to 80% (W/V) and the concentration of the perfluoro-carbon compound being 5 to 30% (W/V), the ratio of the organic iodine compound to the perfluoro-carbon compound being from 0.17:1 to 16:1, and the perfluorocarbon compound in the emulsion having a particle size of 0.05 to 0.3$\mu$.

2. A physiologically isotonic contrast composition for angiography according to claim 1, wherein the perfluorocarbon compound is a mixture of perfluorodecalin and perfluorotripropylamine.

* * * * *